Figure 1:
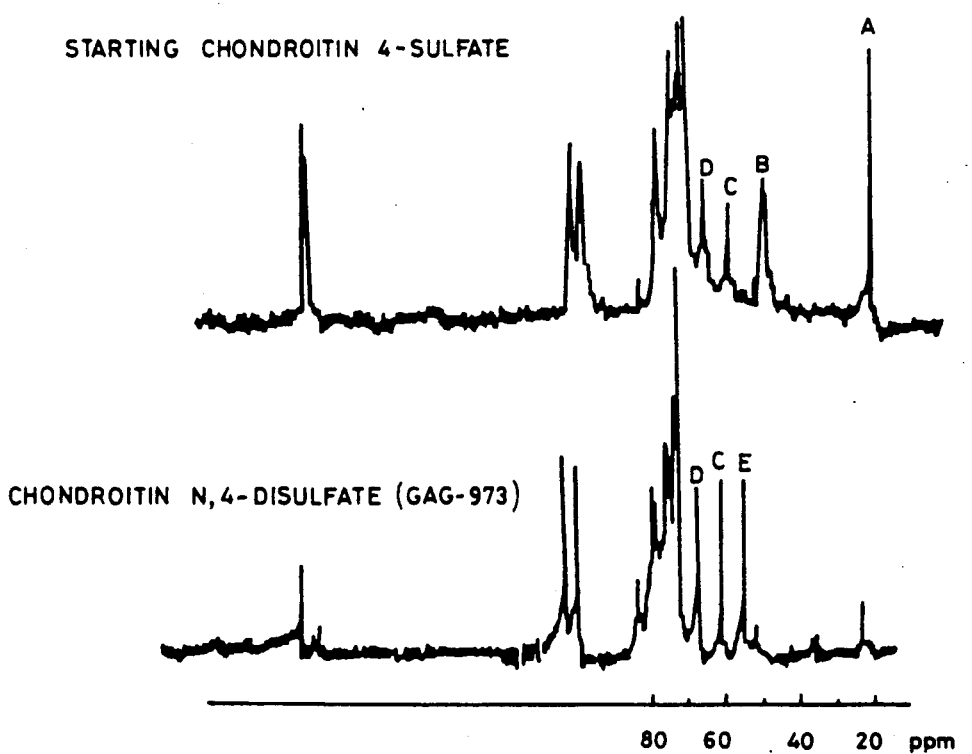

United States Patent [19]

Casu et al.

[11] Patent Number: 5,008,253

[45] Date of Patent: Apr. 16, 1991

[54] SULFOAMINO DERIVATIVES OF CHONDROITIN SULFATES OF DERMATAN SULFATE AND OF HYALURONIC ACID AND THEIR PHARMACOLOGICAL PROPERTIES

[75] Inventors: Benito Casu; Giangiacomo Torri, both of Milan; Annamaria Naggi, Legnano; Marisa Mantovani, Villa Guardia; Rodolfo Pescador, Milan; Roberto Porta, Cernobbio; Giuseppe Prino, Milan, all of Italy

[73] Assignee: Crinos Industria Farmacobiologica SPA, Villa Guardia, Italy

[21] Appl. No.: 346,502

[22] Filed: May 2, 1989

[30] Foreign Application Priority Data

May 2, 1988 [IT] Italy .............................. 20412 A/88

[51] Int. Cl.$^5$ ....................... A61K 31/00; C07H 1/00; C07H 15/00; C08B 37/00

[52] U.S. Cl. .................................. 514/54; 514/62; 536/17.5; 536/18.5; 536/54; 536/55.3; 536/120; 536/122; 536/124

[58] Field of Search ............... 514/54, 62; 536/55.2, 536/55.1, 17.2, 17.5, 17.6, 17.9, 21, 22, 54, 18.5, 55.3, 115, 116, 118, 119, 120, 122, 124

[56] References Cited

U.S. PATENT DOCUMENTS

4,774,231  9/1988  Petitou et al. ....................... 536/118
4,818,816  4/1989  Petitou et al. ....................... 536/118

FOREIGN PATENT DOCUMENTS

838709  6/1960  European Pat. Off. ..

OTHER PUBLICATIONS

Hydrazinolysis of Heparin Ando Ther Glycosaminoglycans, Patrick N. Shaklee and H. Edward Conrad, Biochem. J., vol. 217, 1984, pp. 187–197.

*Primary Examiner*—Ronald W. Griffin
*Assistant Examiner*—Everett White
*Attorney, Agent, or Firm*—Armstrong, Nikaido, Marmelstein, Kubovcik & Murray

[57] ABSTRACT

Novel derivatives are disclosed as obtained from chondroitin sulfate, dermatan sulfate and hyaluronic acid, having a molar ratio between sulfate groups and carboxylic groups like that of heparin and furthermore characterized by possessing, as the heparin, the sulfoamino group at the carbon atom at the 6 position of hexosamine.

The novel compounds show a very remarkable clearing activity in comparison with the starting mucopolysaccharides, this activity being similar and for some derivatives comparable with that of heparin.

Moreover, differently from what normally happens upon sulfating the sulfomucopolysaccharides, the anticoagulating activity of the novel compounds is negligible or anyhow very reduced.

The compounds of the present invention find use in the therapy of arteriosclerosis.

12 Claims, 5 Drawing Sheets

N-DEACETILATED O-SULFATED DERMATAN SULFATE (GAG 986)

SULFOAMINO DERIVATIVES OF CHONDROITIN SULFATES OF DERMATAN SULFATE AND OF HYALURONIC ACID AND THEIR PHARMACOLOGICAL PROPERTIES

The present invention relates to novel derivatives of glycosaminoglycans and more particularly of chondroitin sulfates and of hyaluronic acid. More specifically, within the family of the chondroitin sulfates, the compounds are described which are obtained from chondroitin sulfates A and C and related mixtures, as well as from dermatan sulfate.

The glycosaminoglycans or sulfomucopolysaccharides or simply mucopolysaccharides are polymers very widespread in the organs and tissues of animals. Among them the polymer which has undoubtedly achieved maximum use in the therapeutical field is heparin, a macromolecule characterized by a high content of sulfate groups and possessing anticoagulating, antithrombotic and clearing activity, the latter activity being due to the lipoprotein lipase and to the hepatic lipase.

These peculiar pharmacological activities have stimulated in the past years, (although for a number of aspects these studies are still pending), a great number of investigations in order to clarify the possible relationship between the structure of the polymer and the above mentioned activities (for recent comprehensive papers see B. Casu, Advances Carbohydr. Chem. Biochem. 43 51-134 1985; L. A. Fransson in "The Polysaccharides", G. O. Aspinali Ed. Vol. 3, pp. 337-415 Academia Press, New York 1985).

It has been thus assessed that to the said activities both the sulfoamino group (I. Danishefsky, Fed. Proc. Am. Soc. Exp. Biol. 36 pp. 33-35 1977) and the charge density of the polymer (R. E. Hurst et Alii, in "Chemistry and Biology of Heparin" Elsevier North Holland New York, pp. 29-40 1981; R. E. Hurst et al., J. Clin. Invest. 72 1042-1045 1983; U. Lindhal et al., in Annual Rev. Biochem. 47 pp. 401-406 1978) contribute in a relevant measure.

With reference to the charge density, it has been found that in the heparin it is on the average equal to 2, if it is expressed as the ratio between the moles of sulfate groups and the corresponding moles of carboxylic groups (B. Casu, see above).

It is worth to note that in the past and in the recent times a number of attempts has been carried out to obtain from several glycosaminoglycans, through a reaction of direct sulfation, polymers having property like those of heparin.

For example it is known that the chondroitin sulfates directly subjected to sulfation (K. H. Meyer, Helv. Chim. Acta 75 574-588 1952), or initially N-deacetylated and then sulfated (M. L. Wolfrom, J.A.C.S. 75 1519 1953) acquire anticoagulating properties.

Alternatively, through an initial depolymerization followed by a sulfation at the hydroxyl groups, starting from the heparin itself as well as also from other glycosaminoglycans, it is possible to obtain polymers which are characterized by an antithrombotic activity which is comparable or even greater than that of heparin. However, it is the worth to note that only the derivatives of the latter polysaccharide, among those which are described in the present invention, possess a very reduced anticoagulating activity (EP-A-86401563.1).

It is moreover to be observed that in the literature several methods are reported for the sulfation of glycosaminoglycans, which generally the sulfation of the hydroxyl groups only to be carried out.

As a matter of fact, by means of these methods it is not possible to obtain the selective sulfation of the nitrogen atom in the 2-position of the hexosamine. By adopting particular conditions it is however possible to obtain, as it will be shown hereinafter, the selective sulfation of the hydroxyl groups occuping the polymer chain at the less sterically hindered position.

However, these reactions normally lead to products with a high content of sulfur, wherein the distribution of the sulfate groups among the several positions takes place in a non specific manner.

Said reactions most of time are carried out in heterogeneous phase, usually in anhydrous pyridine and using as the sulfating agent the pyridinesulfuric anhydride adduct or chlorosulfonic acid.

It is also possible to operate in a homogeneous phase, in apolar non aqueous solvents (for example dimethylformamide) and using as the sulfating agent sulfure trioxide or the trimethylamine-sulfur trioxide adduct (J. F. Kennedy, Advances Carbohyd. Chem. Biochem. 29 335-337 1974). E. E. Gilbert "Sulfonation and related reactions" Interscience publisher, New York 1965, pp 354-360; R. G. Schweiger "Polysaccharides sulfates. I Cellulose sulfate with a high degree of substitution" Carbohyd. Res. 21 219 1972: K. Nagasawa et al. "Chemical sulfation of preparations of chondroitin 4 and 6 sulfate and dermatan sulfate. Preparations of chondroitin sulfate E-like materials from chondroitin sulfate" Carbohyd. Res. 158 1983 1986).

The glycosaminoglycans to which the present invention relates are precisely chondroitin sulfate A and C and their mixtures, dermatan sulfate or chondroitin sulfate B and hyaluronic acid, of which the structural formula of the related repeating disaccaride unit is hereinafter reported.

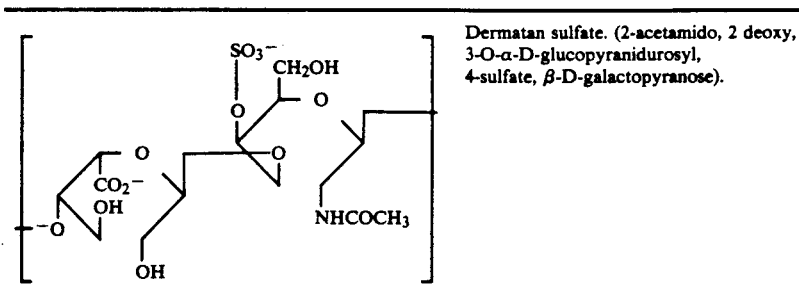

Dermatan sulfate. (2-acetamido, 2 deoxy, 3-O-α-D-glucopyranidurosyl, 4-sulfate, β-D-galactopyranose).

-continued

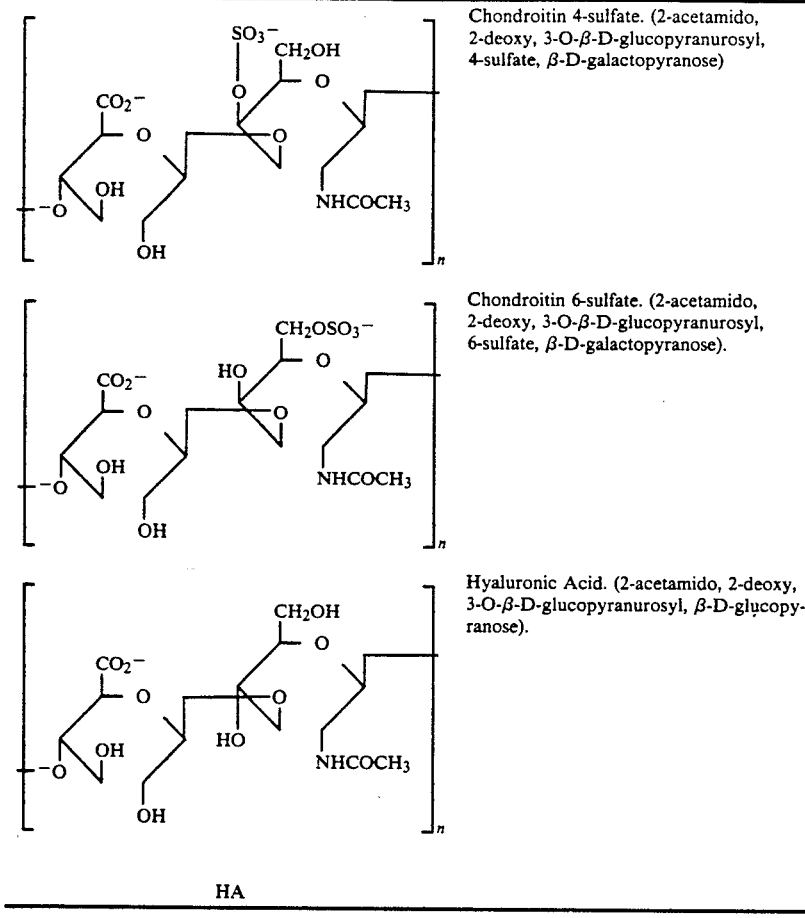

HA

A first object of the present invention thus consists in novel synthetic derivatives of some glycosaminoglycans and exactly of chondroitin sulfate A and C or their mixtures, chondroitin sulfate and hyaluronic acid, obtained by selective N-deacetylation and subsequent sulfation at the nitrogen atom (which in the case of the hyaluronic acid is preceded or followed, as it is disclosed in the examples 6 and 7, by the sulfation at the hydroxyls in the 6-position) so as to obtain polymers which, besides the charge density which is characteristic of the heparin as above defined, have also the nitrogen atom at the position 2 on the hexosamine ring substituted with a sulfate group.

It has moreover been found and it is another object of the present invention that these macromolecules possesses a clearing activity.

The novel polymers, with reference to the above indicated clearing activity and to the said absence of a remarkable anticoagulating activity, are useful as drugs in the therapy of arteriosclerosis. Within the above indicated pharmacological activity as shown by the present compounds, a relevant increase of the activity due to the hepatic lipase is noticed, which in the case of the derivatives of dermatan sulfate and of the chondroitins contributes by fifty percent and more to the lipaemia clearing activity.

As a matter of fact in the pharmacology to the hepatic lipase an important role is attributed as regards the metabolism of lipoproteins and of their influence on the cholesterol catabolism (T. Kuusi et al., FEBS Lett. 104 384 1979; H. Jansen et al., Biochim. Biophys. Res. Comm. 92 53 1980, A. Van Tol et al., Biochim. Biophys. Res. Comm 94 101, 1980; M. Bamberger et al., J. Lipid Res. 24 869 1983; H. Jansen et al., Trends Biochem. Sci. 5 265 1980).

Moreover it has been recently assessed during clinical pharmacological experiments (Jacques D. Barth et al., Atherosclerosi 48 235 1983 and 68 51 1987) that in individuals suffering from heavy complications of arteriosclerosis the serum values of the hepatic lipase are lower than those of normal patients, differently from those of the lipoprotein lipase. These information indicate per sé the potential and the remarkable importance which in the therapy of these diseases the use may have of a drug which, without influencing the haemostasis, would be able to stimulate an effective activity of the hepatic lipase in the blood circuit.

Coming back to the chemical structure of these compounds, it is worth to note that the reactions of N-deacetylation and subsequent selective N-sulfation, which by the way are carried out with per sé known method, do not change the amount and distribution of the sulfate groups which are initially present in the polymer.

It is furthermore to be mentioned, as it will be demonstrated hereinafter, that by other methods already described in the literature for the sulfation of glycosaminoglycans, even in the presence of compounds which are partially or totally N-deacetylated, it is not possible to obtain polymers which, although having the same content of sulfur, have the same distribution of sulfate groups.

The structures which are obtained by carrying out the above reactions on the above said the macromolecules can be synthetically represented with the structural formulas which are hereinafter reported:

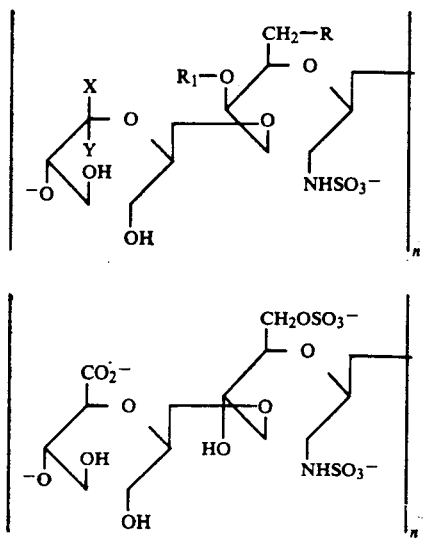

The formula I relates to the derivatives which are obtained starting from chondroitin sulfate A and C respectively, or from their mixtures, and from dermatan sulfate or chondroitin sulfate B; more precisely:

chondroitin 6-sulfate N-sulfate (dimeric unit: 2-sulfoamino, 2-deoxy 3-O-β-D-glucopyranurosyl, 6-sulfate, β-D-galactopyranose): $R=SO_3^- $ $R_1=H$, $Y=H$, $X=COO^-$.

chondroitin 4-sulfate N-sulfate (dimeric unit: 2-sulfoamino, 2-deoxy, 3-O-β-D-glucopyranurosyl, 4-sulfate, β-D-galactopyranose): $R=OH$, $R_1=SO_3^-$, $Y=H$, $X=COO^-$.

dermatan sulfate N-sulfate (dimeric unit: 2-sulfoamino, 2-deoxy, 3-O-α-D-glucopyraniduronosyl, 4-sulfate, β-D-galactopyranose): $R=OH$, $R_1=SO_3^-$, $Y=-COO^-$, $X=H$ The formula II on the contrary relates to the compound obtained from hyaluronic acid (dimeric unit: 2-sulfoamino, 2-deoxy, 3-O-β-D-glucopyraniduronosyl, 6-sulfate, β-D-glucopyranose).

The above dimeric units are repeated within the polymer for a number of times varying between 4 and 52, respectively equivalent, in the case of the corresponding sodium salt, to a molecular weight of about 2,300 and 30,000.

The reactions through which the synthesis of the above compounds has been carried out are per se known in the literature and consist, as regards the chondroitin sulfate, in an initial N-deacetylation carried out by heating in a carious pipe to the temperature of 105° C. the substance with an excess of hydrazine sulfate and anhydrous hydrazine for a time of 6 hours or less (B. A. Dimitrev et al, "Selective cleavage of glycosidic linkages" Carbohyd, Res. 29 451 1973; "Selective cleavage of glycosidic linkages, studies with the model compound benzyl-2-acetamido-deoxy-6-O-D-mannopyranosyl-D-glucopyranoside" Carbohyd. Res. 30 45 1973; "Selective cleavages of glycosidic linkages, studies with the O-specific polysaccharide from *Shigella disenteriae* Type 3" Carbohyd. Res. 40 365 1975). The subsequent reaction of selective N-sulfation is carried out in aqueous phase at pH 9, using an excess of the sulfating agent trimethylamine-sulfuric anhydride (L. Levy et Alii, "Chemical and pharmacological studies on N-resulfated heparin" Proc. Soc. Exp. Biol. Med. 109 901 -1982; Y. Ynoue et al, "Selective N-desulfation of heparin with dimethyl sulfoxide containing water and methanol" Carbohyd. Res. 46 87 1976). It is noticeable that the N-deacetylation reaction can be repeated a second time so as to lower the content of acetyl groups to the desired level when it has not been possible in the first step.

It is now to be pointed out that the $^{13}$C NMR spectra herein enclosed and particularly those of the FIGS. 1, 2, 3 and 5, clearly show that under the adopted conditions it takes place in an almost complete manner not only the N-deacetylation but also the subsequent N-sulfation, as it is shown by the peak relating to the sulfoamino group (about 55 ppm) and from the small importance of the peak corresponding to the acetylamino group (25 ppm).

It is furthermore to be observed that as regards the preparation of compounds having low molecular weight, the glycosaminoglycans may, if necessary, undergo a preliminary reaction of the depolymerization which can be carried out with per se known methods, either of chemical or of enzymatic nature (L.A. Fransson "Mammalian glycosaminoglycans" in G.O. Aspinall "The polysaccharides", Academic Press vol. 3 337 1985).

Lastly, as regards the hyaluronic acid, the sulfation at the oxygen atom can be carried out before the depolymerization or, as it is preferable, after this step. The sulfation reaction is carried out selectively at the hydroxyl of the carbon atom 6, using methods known in the prior art, such as for example the reaction in dimethyl formamide using the triethylamine-sulfurtrioxide adduct (example 4) of the sulfation with a mixture of sulfuric acid-chlorosulfonic acid (A. Naggi et al, "Supersulfated heparin fragments, a new type of low-molecular weight heparin". Biochem. Pharmacol. 36, No. 17, p. 1985 (1987).

The chemical parameters which characterise the polymers obtained through the above reaction are the following (the data have been calculated on dry basis and relate to the corresponding sodium salt of these substances):

| | | |
|---|---|---|
| Sulfonic sulfur: | 8.0–12% | preferably 9.5–11.4% |
| Sulfates/carboxyls: | 1.5–2.3 | preferably 1.8–2.1 |
| Residual N-acetyl groups: | 3% | preferably 1% |
| *Molecular weight: | $2,3–30 \times 10^3$ | preferably $3–15 \times 10^3$ |

In order to demonstrate that by the methods used for the sulfation of the hydroxyls it is not possible to obtain, starting from the above sulfomucopolysaccharides, compounds having the chemical properties described in the present invention, a sulfation has been carried out on a preparation of dermatan sulfate which previously had been selectively N-deacetylated, by reaction with trimethylamine-sulfur trioxide adduct in dimethylformamide, according to the disclosure of the EP-A-86401563.1.

The polymer, as it is required by the process described in the above patent application, has been previously converted into the corresponding salt with a quaternary ammonium cation (triethylammonium).

The experiment and the obtained results are described in the example 4.

It has been assessed that in the range (1.5-2.3) of the ratio between the sulfate groups/carboxylic groups of interest for the present invention the sulfation reaction takes place under the above conditions almost exclusively at the oxygen atom of the alcoholic group which in the polymer chain has the less sterically hindered position, namely that bound to the carbon atom positioned at position 6 in the galactosamine ring.

It has been moreover assessed (example 5) that also adopting the sulfation conditions reported by M. L. Wolfrom in J.A.C.S. 75 1519 (1953) (pyridine+chlorosulfonic acid) and even starting from a preparation of dermatan sulfate previously N-deacetylated, it is not possible to have the reaction occurring at the ammonium group of the galactosamine.

Figure 5:
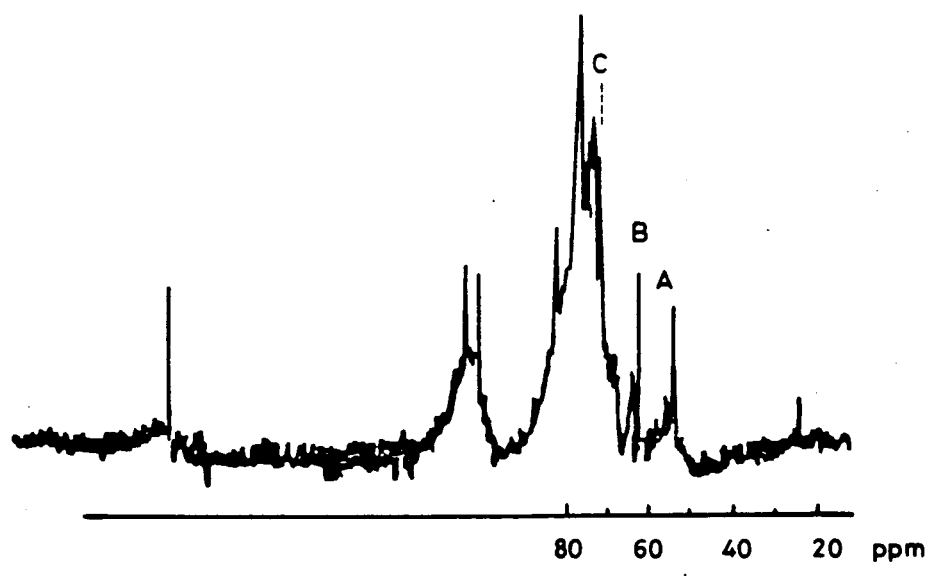

As a matter of fact, also in this case it has been demonstrated that the reaction takes place at the hydroxyl groups; more precisely the sulfation takes places at the hydroxyl at position 6 of galactosamine and that at the position 2 of the hyaluronic acid (FIG. 5).

From the preceeding information it is evident that the sulfated product of the present invention are obtained only under particular sulfation conditions.

As regards the method which have been used to evaluate the pharmacological properties of the novel derivatives of the invention, the anticoagulating activity has been assessed in vitro according to the method USP XX, using as the reference standard the third international standard of heparin.

The clearing activity induced both by lipoprotein lipase and by hepatic lipase has been assessed according to the method described in the paper by R. Pescador et al., Biochem. Pharmacol. 36 4 253 1987.

For the reasons which are hereinafter stated with reference to table I, the results obtained for the activity of the lipoprotein lipase and of the hepatic lipase (expressed in micromoles of free fatty acids) relating to the lowest and to the highest among the administered doses have been reported.

The data which have been obtained in the previous experiments, are reported in table I in which a comparison is carried out with those relating to the starting glycosaminoglycans. For these substances however no statistically significant relationship between the administered dose and the corresponding activity has been assessed. For these reasons in the table I the results have been reported corresponding to the lowest dose and to the highest dose among those administered, in order to render anyhow possible a comparison.

From the table I it is evident the relevant increase of the clearing activity of the novel compounds in comparison with that of the starting sulfomucopolysaccarides.

Moreover, it is observed that in the case of the derivatives of chondroitins and of the dermatan sulphate the hepatic lipase contributes to the total clearing activity by fifty percent and more.

It is worth to note that, with reference to the data reported in the indicated table, at the dose of 1.25 mg/kg, the activity of the hepatic lipase is similar and in the case of the compounds obtained from dermatan sulfate and from hyaluronic acid is comparable with the corresponding one of heparin at the dose of 1.4 mg/kg.

In the case of the derivative of hyaluronic acid the activity of lipoprotein lipase is comparable with that of heparin.

In the table II it is demonstrated that by introducing in a N-deacetylated and subsequently N-sulfated derivative of chondroitin sulfate (in the subject case chondroitin sulfate A+C) a sulfate group at a hydroxyl (with reference to the relating unit, see the previous structural formula) a relevant increase of anticoagulating activity is obtained which is three times greater than that of the starting polymer.

In the table III the data are illustrated relating to the anticoagulating activity of a sample of dermatan sulfate having sulfate groups substituted for some hydroxyl functions (GAG 938) and furthermore characterized by having a ratio between sulfate groups and carboxylic groups of 2, and consequently formally falling within the range foreseen by the present invention.

The above said table demostrates that the sulfation at the oxygen atom does not produce the same effect, as regards the anticoagulating activity, as the like reaction at the nitrogen atom of galactosamine.

As a matter of fact in the case of the GAG 938 derivative this activity is at least double with respect to the starting polymer and is anyhow greater than that of the corresponding derivative wherein the sulfation has on the contrary occurred at the nitrogen atom of the galactosamine (GAG 944 IV, table I).

These examples confirm that for the therapeutic use as drugs having clearing activity of sulfate derivatives of chondroitin sulfates, of dermatan sulfate and of hyaluronic acid, when these compounds have no side effects of haemostasis, two structural requirements are essential, namely the selective sulfation at the nitrogen atom in the position 2 of the pyranose ring of hexosamine and the ratio between moles of sulfate groups and of carboxylic groups, which must be within the range for seen by the present invention.

As a confirmation of the above structural requirements which as stated are critical in order to obtain compounds having an evident clearing activity without undesired effects on the coagulation, it is worth to note that by acting on a polymer which does not contain sulfate groups at the hydroxyls, as for example hyaluronic acid, a N-sulfation reaction at the nitrogen atom in the position 2 of hexosamine according to the process described in the example 6, a substance is obtained (GAG 1045) having a very reduced clearing activity with respect to the corresponding derivatives in which also the hydroxyl in the 6-position is substituted for with a group $-OSO_3$.

TABLE I

| Substances | $SO_3^-/COO^-$ | Anticoagulating activity USP (I.U./mg) | doses mg/Kg iv | Clearing activity (micromoles FFA) LPL | Hepatic Lipase |
|---|---|---|---|---|---|
| Chondroitin 4-sulfate (GAG 920) | 1 | <10 | 5-20 | 0.25-0.86 | 3.99-3.51 |
| Chondroitin N,4-disulfate (GAG 973) | 2.2 | <10 | 1.25-5 | 0.58-2.16 | 2.64-6.30 |
| Chondroitin 6-sulfate (GAG 921) | 1 | <10 | 5-20 | 0.30-0.82 | 3.27-2.98 |
| Chondroitin N,6-disulfate | 2.1 | <10 | 1.25-5 | 0.82-3.56 | 4.06-6.07 |

TABLE I-continued

| Substances | $SO_3^-/COO^-$ | Anticoagulating activity | | Clearing activity (micromoles FFA) | |
|---|---|---|---|---|---|
| | | USP (I.U./mg) | doses mg/Kg iv | LPL | Hepatic Lipase |
| (GAG 974) Dermatan sulfate (GAG 968) | 1.1 | <10 | 5-20 | 0.59-0.75 | 4.57-3.98 |
| Dermatan sulfate N-sulfate (GAG 944 IV) | 1.8 | 13 | 1.25-5 | 4.28-19.44 | 5.51-16.15 |
| Acid hyaluronic (GAG 1039) | — | <10 | 5-20 | 0.15-0.25 | 1.12-2.03 |
| Acid hyaluronico N,6-disulfate (GAG 1046) | 1.8 | <10 | 1.25-5 | 9.24-21.17 | 4.47-7.53 |
| (HEP 024) | | 136.9 | 0.35-1.4 | 4.61-14 | 2.56-5.93 |

Note:
the wording "N,4-disulfate or N,6-disulfate" means that in the hexosamine, which together with the hexuronic acid is part of the repeating disaccaride unit of these polymers, the nitrogen atom substituted at the carbon atom in the position 2 is substituted for with a group-$SO_3^-$ and the hydroxyls positioned at the carbon atom in position 4 or in position 6 of the ring are substituted with a group —$OSO_3$—

TABLE II

| Substances | $SO_3^-/COO^-$ | Anticoagulating Activity | | Clearing activity (micromoles FFA) | |
|---|---|---|---|---|---|
| | | USP I.U./mg | DOSES mg/Kg iv | LPL | Hepatic Lipase |
| Chondroitin sulfate A + C (GAG 267) | 1 | 10 | 5-20 | 0.25-0.50 | 1.97-2.76 |
| Chrondroitin sulfate A + C N-sulfate and further sulfated at the oxygen (GAG 952) | 2.7 | 31.7 | 0.625-2.5 | 7.92-22.45 | 6.86-13.46 |

TABLE III

| Substances | $SO_3^-/COO^-$ | Anticoagulating Activity | | Clearing Activity (micromoles FFA) | |
|---|---|---|---|---|---|
| | | USP I.U./mg | Doses mg/Kg iv | LPL | Hepatic Lipase |
| Dermatan Sulfate (GAG 968) | 1 | <10 | 5-20 | 0.59-0.75 | 4.57-3.98 |
| Dermatan Sulfate O-sulfate (GAG 938) | 2 | 20 | 0.313-1.25 | 3.16-12.99 | 3.80-9.06 |

TABLE IV

Clearing activity if hyaluronic acid (GAG 1039), of the corresponding derivative N-deacetylated and N-sulfated (GAG 1045) and of the derivative obtained by sulfation at the hydroxil group in the position 6 of glucosamine (GAG 1046)

| Substance | $SO_3^-/COO^-$ | doses (mg/Kg i.v.) | Clearing activity (micromoles FFA) | |
|---|---|---|---|---|
| | | | LPL | Hepatic Lipase |
| GAG 1039 | — | 5-20 | 0.15-0.25 | 1.12-2.03 |
| GAG 1045 | 0.9 | 5-20 | 0.48-1.88 | 1.21-0.86 |
| GAG 1046 | 1.8 | 1.25-5 | 9.24-21.17 | 4.47-7.53 |

The substances according to the presente invention can be administered in form of their pharmacologically acceptable salts, such as, as a non limiting example, the corresponding salts with alkali and alhaline earth metals, for example sodium and calcium salts.

The foreseen pharmaceutical forms are the standard ones: sterile and apyrogenic solutions in vials and lyophilized preparations packaged in sterile bottles to be dissolved upon administering in the solvent for the administration by parenteral and subcutaneous route; tablets, gelatin or gastroresistant capsules, granulates for the oral administration.

The solutions for parenteral administration may contain 1 to 250 mg/ml of active principle, preferably 1 to 150 mg/ml, whereas the compositions for oral use have a content of active principle as a unitary dose of 1-500 mg.

The daily posology may vary from 1 to 2,000 mg, preferably from 1 to 500 mg.

Example 1

1 g of chondroitin 4-sulfate (ratio sulfate groups/carboxylic groups=1.07; identification n. GAG 920; m.w. 12,000) is admixed with 0.325 g of anhydrous hydrazine, directly in a carius pipe which is immediately after tightly sealed.

The N-deacetylation reaction is carried out by heating the pipe to 105° C. for 5 hours.

At the end the liquid phase is evaporated under reduced pressure making use of subsequent addition of toluene to promote the removal of hydrazine.

The residue is taken with water and the alkalinity is neutralized by adding 1M HCl and by cooling in water and ice bath.

The solution is then dialyzed with distilled water through dialysis membranes of 3500 D (Thomas dialyzer tubing 3787-H47).

The solution is then evaporated under reduced pressure thus recovering 700 mg of chondroitin 4-sulfate N-deacetylated (identification No. GAG 957).

1 g of the product is dissolved in 20 ml of distilled water, the pH of the resulting solution being adjusted to 9 by means of few drops of 2N NaOH.

The solution is heated to 55° C. and under stirring 1 g of the trimethylamine-sulfur trioxide complex is added together with about 900 mg of sodium bicarbonate, in order to restore the alkaline pH. Subsequently, at 4-hour intervals (at the fourth and eight hour) the addition of 1 g of reactant and of 900 mg of the salt is repeated.

After 16 hours the reaction is stopped by cooling the reaction mixture to room temperature.

Then the solution is dialyzed, by using the same above indicated membrane but substituting for the distilled water a 0.5M solution of sodium chloride. By evaporation under reduced pressure there are obtained 1.1 g of chondroitin sulfate N-sulfate with a ratio sulfate/carboxylic groups=2.2; m.w. 8000; identification number: GAG 973). The $^{13}$C NMR spectrum (FIG. 1) shows an attenuated signal at 25 ppm (group-CH3, letter A), a signal at about 55 ppm (letter E) corresponding to the carbon atom at the position 2 of the galactosamine bearing the group NH—SO3. There are furthermore seen, as in the starting polymer, a signal at about 60 ppm (letter C) corresponding to the carbon atom in the position 6 of the galactosamine bearing a hydroxyl group, and at about 70 ppm (letter D) relating to the carbon atom in the position 4 of the galactosamine bearing a sulfate group.

The signal indicated in FIG. 1 with the letter B corresponds to the carbon atom in the position 2 of the galactosamine bearing as substituent the group —NH—CH3.

EXAMPLE 2

1 g of chondroitin 6-sulfate (ratio of sulfate/carboxylic group=1, identification No. GAG 921, m.w. 18.000) is admixed with the same amount of hydrazine sulfate indicated in the above example. The N-deacetylation reaction is carried out as above described.

Then the N-sulfation is carried out obtaining 1.2 g of final product (identification N. GAG 974) having a ratio between sulfate groups and carboxylic groups of 2.1, m.w. 15.000.

Figure 2:
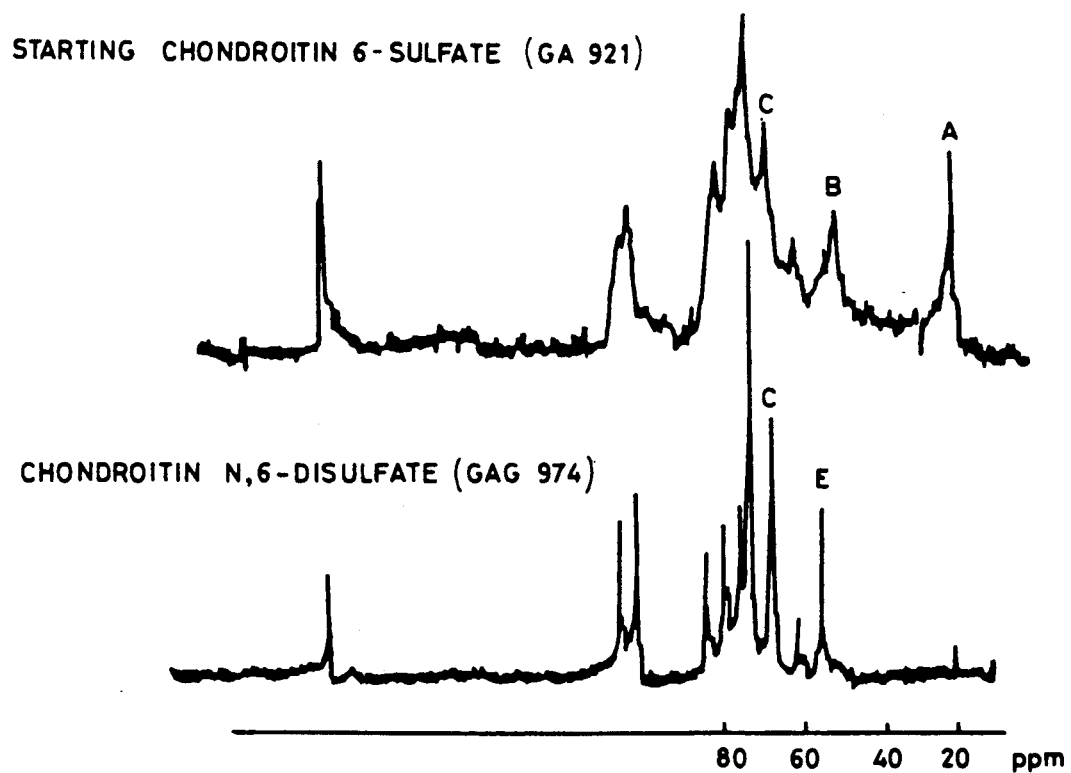
Figure 3:
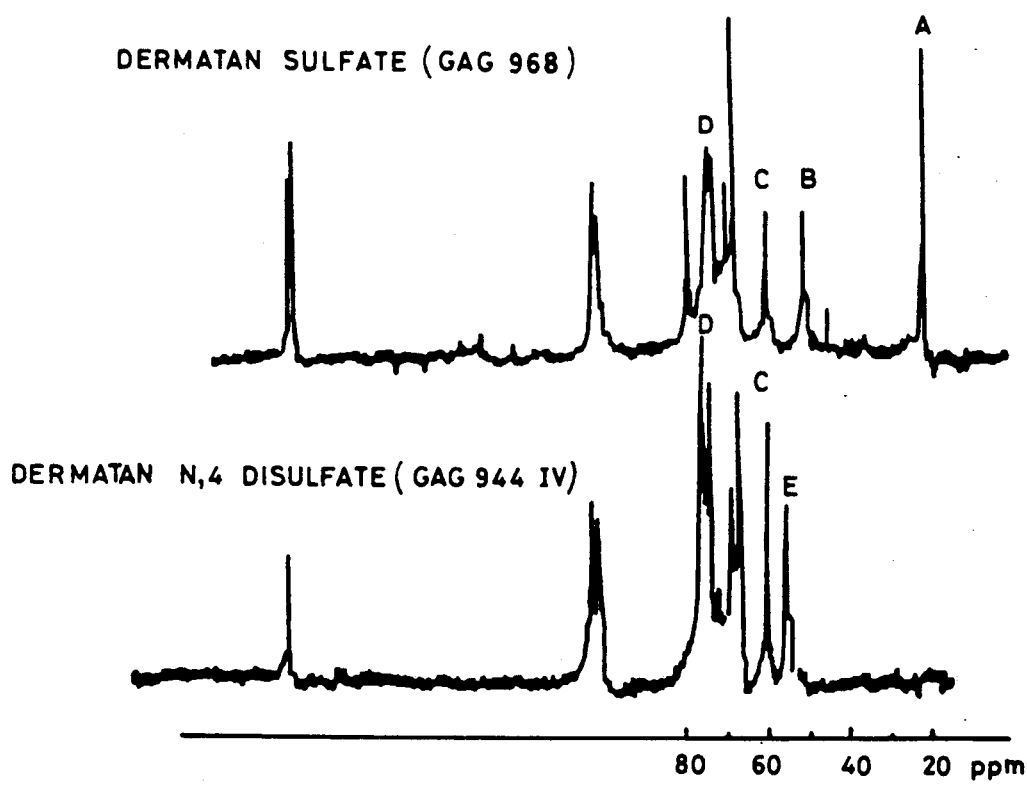

The spectrum, reported in FIG. 2, apart from the signals common to that showed in FIG. 1 as regards the almost total absence of N-acetyl groups and the appearance of the signal corresponding to the sulfoamino group, shows at about 70 ppm the signal (letter C) of the carbon atom in the position 6 of the galactosamine bearing the sulfate group.

EXAMPLE 3

1 g of dermatan sulfate (ratio between sulfate groups and carboxylic groups of 1.1; identification n. GAG 968; m.w. 9000) is subjected to the N-deacetylation reaction and subsequent N-sulfation.

There are obtained 695 mg of the corresponding derivative. The substance (identification n. GAG 944 IV) has a sulfate groups/carboxylic groups ratio=1.8, m.w. 6000.

The $^{13}$C NMR spectrum (FIG. 3) shows, as in the starting substance, one peak at 60 ppm (letter C) corresponding to the carbon atom in the position 6 of the galactosamine bearing a hydroxyl group, one a peak at 55 pm (letter E) relating to the carbon atom in the 2-position of the galactosamine bearing a group NH—SO3 and lastly, likewise the dermatan sulfate, one peak at 77 ppm (letter D) corresponding to the carbon atom in the position 4 of the same ring bearing a sulfate group.

EXAMPLE 4

This example relates to the sulfonation carried out on one sample of N-deacetylated dermatan sulfate, prepared according to the previous example, according to the E. P. Application No. 86401563.1.

The N-deacetylated sample (1 g) is converted into the corresponding acidic form by dissolving the substance in 10 ml of distilled water and admixing with Amberlite IR 120 (form H+). The resin is removed by centrifugation and the pH of the solution is brought to the value of 5 by means of a 10% w/v solution of triethylamine in ethanol. The solution is extracted with ether.

The aqueous phase is lastly lyophilized. 1 g of the obtained salt (salt of N-deacetylated dermatan sulfate with triethylammonium) is dissolved in 140 ml of dimethylformamide. It is cooled to 0° C. and 10 g of the trimethylamine-sulfur trioxide adduct, previously dissolved in 60 ml of dimethylformamide, are added.

The reaction is carried out at the indicated temperature for one hour.

Then water cooled to +5° C. is added, the pH is rapidly brought to 9 by adding 5N NaOH and the product is precipitated by adding 600 ml of ethanol saturated with sodium acetate. During this phase the temperature is constantly maintained at +5° C. It is filtered, dissolved again in water and dialyzed against distilled water, using the above mentioned dialysis membrane.

900 mg of product (identification n. GAG 941) are obtained having a ratio sulfate groups/carboxylic group=1.5.

Figure 4:
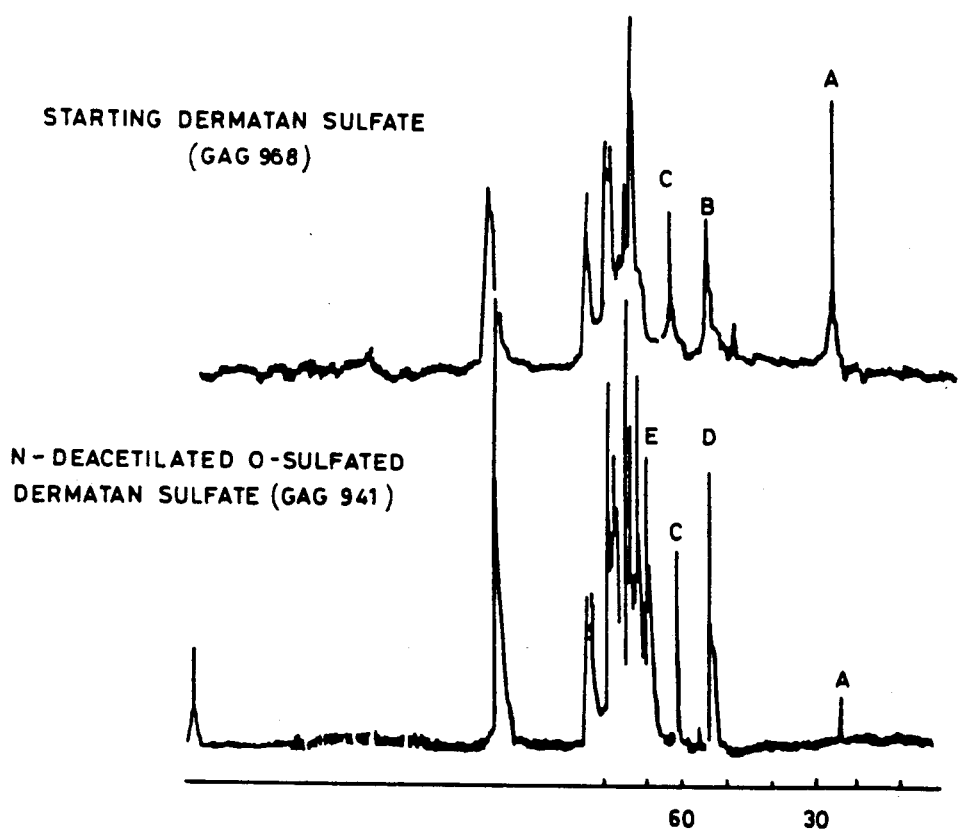

The NMR spectrum (FIG. 4) shows an intense signal at about 50 ppm (letter D) corresponding to the carbon atom in the position 2 of the galactosamine and bearing the primary amino group (—NH2), one signal between 60 and 65 ppm (letter C) corresponding to the carbon atom in the position 6 of the galactosamine bearing a free hydroxyl and lastly a signal between 65 and 70 ppm (letter E) corresponding to the carbon atom in the position 6 with a substituent-SO3.

The peaks indicated by the letters A and B respectively maintain the meaning attributed thereto in the FIG. 1.

EXAMPLE 5

Sulfation of dermatan sulfate previously N-deacetylated according to the method described by M. L. Wolfrom, J.A.C.S. 75 1519 1953 (pyridine+chlorosulfonic acid).

1 g of N-deacetylated dermatan sulfate are dissolved in 20 ml of distilled water and then precipitated by adding 60 ml of methanol. The precipitate is dried.

In a flask maintained in nitrogen atmosphere, provided with condenser and dropping funnel, there are initially charged 30 ml of anhydrous pyridine at 0° C. By maintaining said temperature in the liquid there are slowly dropwise added 4 ml of chlorosulfonic acid. When the addition is completed, through the same inlet a suspension, previously cooled at 0° C., of N-deacetylated dermatan sulfate in anhydrous pyridine is quickly introduced.

The mixture is moderately heated up to room temperature and then rapidly to 100° C., the reaction being maintained at that temperature for one hour.

The mixture is cooled, the superanatant liquid is decanted and a portion of 20 ml of distilled water is added. The solution is neutralized with 5N NaOH.

Then it is dialyzed against distilled water. Most of the liquid is evaporated under a reduced pressure at 35° C. by means of methyl alcohol and then lyophilized.

There are obtained 750 mg of product (identification n. GAG 986), having a ratio between sulfate groups and carboxylic group of 1.3.

The NMR spectrum (FIG. 5) shows a signal at about 50 ppm (letter A) corresponding to the carbon atom in the position 2 of the galactosamine bearing the group —NH₂, one signal at about 60 ppm (letter B) corresponding to the carbonato in the position 6 bearing a hydroxil group and one peak at 74 ppm (letter C) corresponding to the carbon atom in the position 2 of the ring of the iduronic acid bearing a sulfate group.

EXAMPLE 6

Synthesis of the hyaluronic acid N, 6-disulfate 1 g of the compound previously depolymerized (GAG 1039) and having molecular weight of 15,000, is subjected to the N-deacetylation reaction according to the example 1.

Then N-sulfation is carried out as described, leading to 800 mg of N-sulfate compound.

The next reaction of O-sulfation at the carbon atom in the 6-position of the glucosamine is carried out according to the conditions already indicated in the previous example 4 as regards the like reaction of N-deacetylated dermatan sulfate leading to 650 mg of the foreseen compound (GAG 902), m.w. 7000, having a ratio between sulfate groups and carboxylic groups of 1.9.

The $^{13}$C NMR spectrum shows a signal at about 55 ppm corresponding to the carbon atom in the 2-position of the glucosamine bearing a group NH—SO₃ and a signal at about 70 ppm corresponding to the carbon atom in the position 6 of the glucosamine bearing a sulfate group.

EXAMPLE 7

Synthesis of hyaluronic acid N, 6-disulfate. The previously example is repeated as regard the N-deacetylation and subsequent N-sulfation. The derivative which is obtained (GAG 1045, 0.96 g) has ratio sulfate/carboxyl groups of 0.9. The next reaction of sulfation at the oxygen atom in the 6-position of the glucosamine is on the contrary carried out by using a mixture of sulfuric acid and chlorosulfonic acid (A. Naggi et al, Biochem. Pharmacol. 36 12 1895 1987).

20 ml of 95% H₂SO₄ and 10 ml of HClSO₃ are admixed in a flask at −4° C. 1 g of N-deacetylated and N-sulfated hyaluronic acid, previously dried, is added to the liquid phase maintained under stirring, at the same above mentioned temperature. The reaction is continued for one hour at −4° C. and for further 60 minutes at 25° C.

The sulfation is then terminated by pouring the solution in 500 ml of ethyl ether at −4° C. The precipitate is filtered, dissolved in 20 ml of distillated water and the obtained solution is added with 0.5N NaOH until the reaction pH is neutral.

It is dialized against distilled water and the product is recovered by evaporation under reduced pressure followed by lyophilization. There are obtained 900 mg (GAG 1046) of a compound having a ratio between sulfate groups and carboxylic groups of 1.8, m.w. 8000. The $^{13}$C NMR spectrum is not different, as regards the distribution of the sulfate groups, from that reported for GAG 902.

EXAMPLE 8

Synthesis of GAG 952 (chondroitin sulfate A+C, N-deacetylated and subsequently sulfated both at the nitrogen atom and at the oxygen atom). 1.5 g of chondroitin sulfate A+C are treated as described in the example 1, giving 1.3 g of product in which the nitrogen atom bound to the carbon atom in the position 2 of the galactosamine is almost quantitatively substituted with a sulfate group.

The next sulfation is carried out as described for the sulfation at the oxygen atom described in the previous example 7.

There are obtained 1.3 g of product having a ratio between sulfate and carboxylic groups of 2.7.

EXAMPLE 9

Synthesis of GAG 938 (dermatan sulfate sulfated at the hydroxyl groups of the chain 1 g of dermatan sulfate, GAG 968 is sulfated under the conditions described in the example 7, with respect to the sulfation at the carbon atom in the 6-position of the glucosamine. There are obtained 0.9 g of a product having a ratio sulfate groups/carboxylic groups=2. The $^{13}$C NMR spectrum shows at about 25 ppm an intense signal corresponding to the carbon atom in the 2-position of galactosamine bearing a group NH—CH₃ and a weak signal at about 50 ppm corresponding to the same carbon atom bearing a primary amino function —NH₂.

We claim:

1. Synthetic sulfoamino derivatives of glycosaminoglycans selected from the group consisting of chondroitin sulfates A and C, their mixtures, dermatan sulfate and chondroitin sulfate B, the dimeric units of which have the following formula:

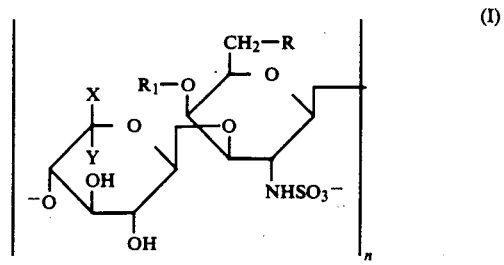

wherein R represents OH, SO₃⁻, R₁ represents H, SO₃⁻, Y represents H, COO⁻, and X represents H, COO⁻.

2. Synthetic sulfoamino derivatives of the hyaluronic acid, the dimeric units of which have the formula:

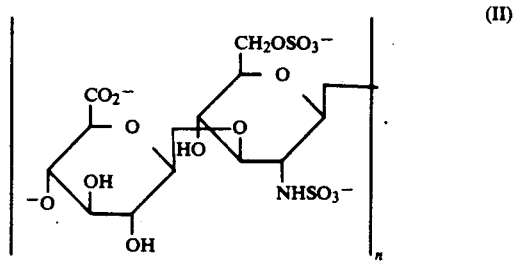

3. Synthetic derivatives according to claims 1 or 2, characterized by the following chemical parameters calculated on dry basis and referred to the corresponding sodium salt:

| | |
|---|---|
| sulfonic sulfur | 8.0–12% |
| sulfate/carboxylic groups | 1.5–2.3 |
| residual N-acetyl groups | <3% |
| molecular weight | 2.3–30 × 10³ |

4. Synthetic derivatives according to claim 3, characterized in that said parameters are included in the following ranges:

| | |
|---|---|
| sulfonic sulfur | 9.5–11.4% |
| sulfate/carboxylic groups | 1.8–2.1 |
| residual N-acetyl groups | <1% |
| molecular weight | 3–15 × 10³ |

5. A process for the preparation of the derivatives according to claim 1 or 2, characterized in that a first N-deacetylation step in carried out by heating the starting glycosaminoglycan to the temperature of 105° C. with an excess of hydrazine sulfate and anhydrous hydrazine for a time not greater than 6 hours and a subsequent step of selective N-sulfation is carried out in aqueous medium at pH 9 with an excess of sulfating agent.

6. A process according to claim 5, characterized in that said sulfating agent is selected from the group consisting of triethylamine-sulfuric anhydride and chlorosulfonic acid.

7. A process according to claim 5, characterized in that said N-deacetylation reaction is carried out in a number of steps until the content of acetyl groups is brought to the level required for the next N-sulfation step.

8. A process according to claim 5, characterized in that before said N-deacetylation step a preliminary depolymerization step is carried out.

9. A process according to claim 8, characterized in that said depolymerization step is carried out before the N-sulfation step.

10. Pharmaceutical composition, comprising, a glycosaminoglycan derivative according to claims 1 or 2, together with pharmaceutically acceptable excipients.

11. Pharmaceutical compostion according to claim 10, having lipaemia clearing activity.

12. Pharmaceutical composition according to claim 10, characterized in that said active ingredient is contained in a unitary dose of 1–500 mg.

* * * * *

UNITED STATES PATENT AND TRADEMARK OFFICE
CERTIFICATE OF CORRECTION

PATENT NO. : 5,008,253

DATED : April 16, 1991

INVENTOR(S) : CASU et al

It is certified that error appears in the above-identified patent and that said Letters Patent is hereby corrected as shown below:

Between columns 1 and 2, delete the formula "

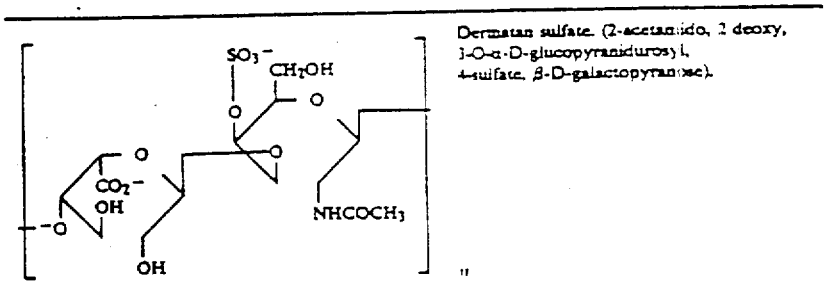

and substitute therefor --

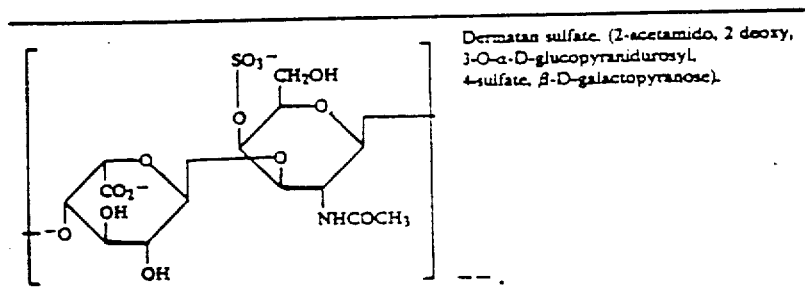

--.

UNITED STATES PATENT AND TRADEMARK OFFICE
CERTIFICATE OF CORRECTION

PATENT NO. : 5,008,253

DATED : April 16, 1991

INVENTOR(S) : CASU et al.

It is certified that error appears in the above-identified patent and that said Letters Patent is hereby corrected as shown below:

Between columns 3 and 4, delete the formulae "

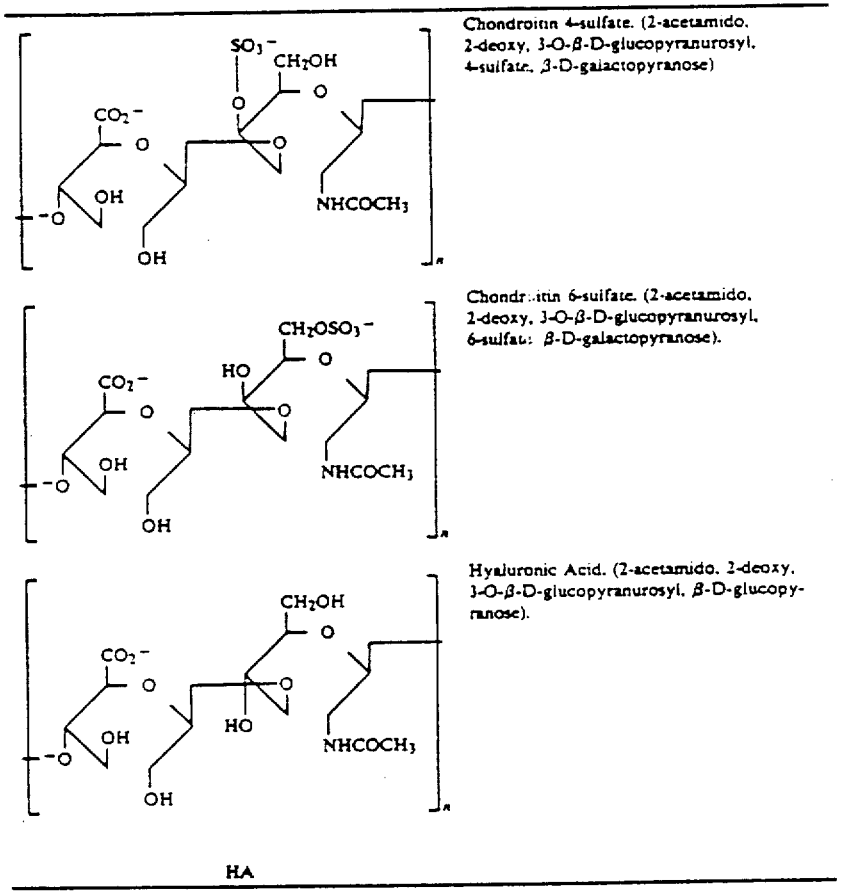

"

UNITED STATES PATENT AND TRADEMARK OFFICE
CERTIFICATE OF CORRECTION

Page 3 of 5

PATENT NO. : 5,008,253
DATED : April 16, 1991
INVENTOR(S) : CASU et al

It is certified that error appears in the above-identified patent and that said Letters Patent is hereby corrected as shown below:

and substitute therefor --

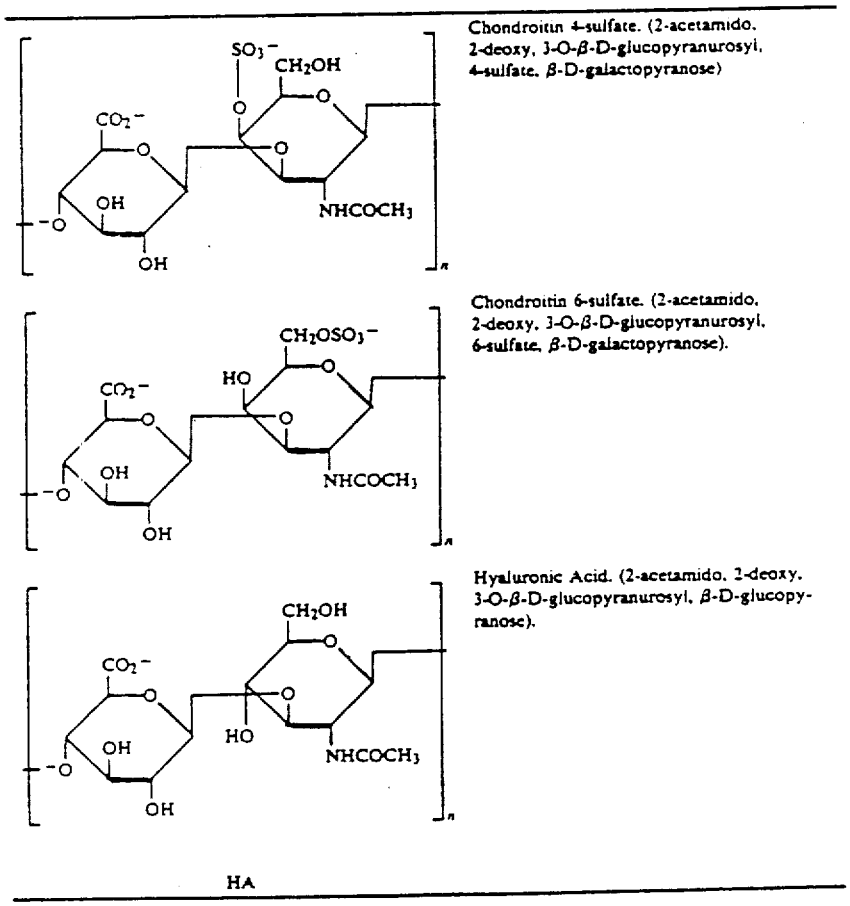

--.

UNITED STATES PATENT AND TRADEMARK OFFICE
CERTIFICATE OF CORRECTION

PATENT NO. : 5,005,253

DATED : April 16, 1991

INVENTOR(S) : CASU et al

It is certified that error appears in the above-identified patent and that said Letters Patent is hereby corrected as shown below:

Column 5, delete the formulae "

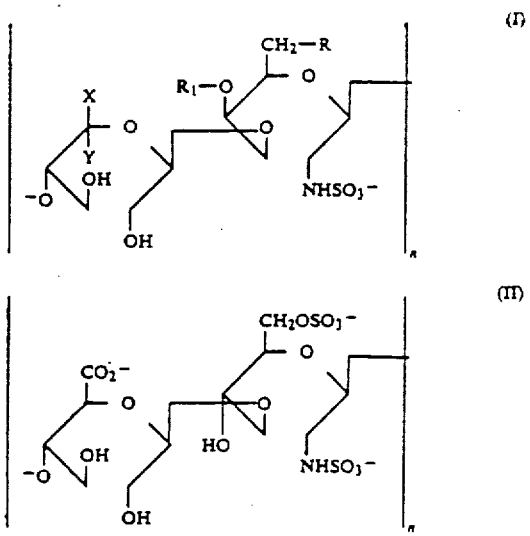

"

UNITED STATES PATENT AND TRADEMARK OFFICE
CERTIFICATE OF CORRECTION

PATENT NO. : 5,008,253
DATED : April 16, 1991
INVENTOR(S) : CASU et al

It is certified that error appears in the above-identified patent and that said Letters Patent is hereby corrected as shown below:

and substitute therefor--

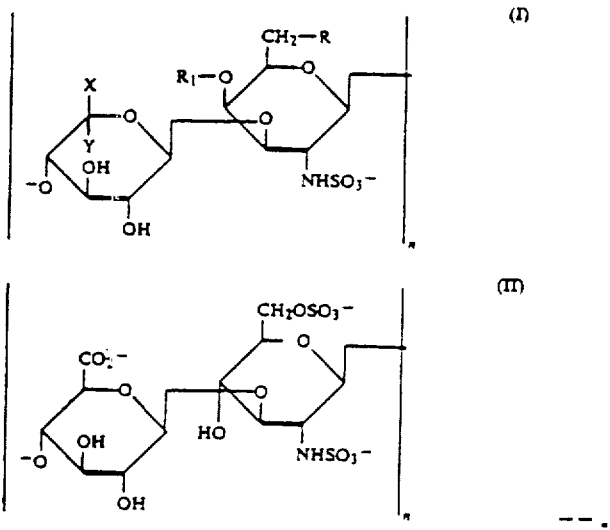

Signed and Sealed this

Thirteenth Day of October, 1992

Attest:

DOUGLAS B. COMER

Attesting Officer

Acting Commissioner of Patents and Trademarks